United States Patent
Kn

(10) Patent No.: US 9,776,013 B2
(45) Date of Patent: Oct. 3, 2017

(54) SYSTEM FOR ANALYZING ENERGY DELIVERED TO ECG DEVICE FROM DEFIBRILLATOR

(71) Applicant: GENERAL ELECTRIC COMPANY, Schenectady, NY (US)

(72) Inventor: Manjunatha Kn, Bangalore (IN)

(73) Assignee: General Electric Company, Schenectady, NY (US)

( * ) Notice: Subject to any disclaimer, the term of this patent is extended or adjusted under 35 U.S.C. 154(b) by 177 days.

(21) Appl. No.: 14/735,590

(22) Filed: Jun. 10, 2015

(65) Prior Publication Data
US 2016/0174896 A1 Jun. 23, 2016

(30) Foreign Application Priority Data
Dec. 23, 2014 (IN) ............................ 6496/CHE/2014

(51) Int. Cl.
| | |
|---|---|
| *A61N 1/39* | (2006.01) |
| *A61B 5/0402* | (2006.01) |
| *A61B 5/044* | (2006.01) |
| *A61B 5/00* | (2006.01) |

(52) U.S. Cl.
CPC .......... *A61N 1/3975* (2013.01); *A61B 5/0402* (2013.01); *A61B 5/044* (2013.01); *A61N 1/3937* (2013.01); *A61B 5/6823* (2013.01); *A61B 2560/0214* (2013.01); *A61B 2560/0266* (2013.01)

(58) Field of Classification Search
None
See application file for complete search history.

(56) References Cited

U.S. PATENT DOCUMENTS

| | | | |
|---|---|---|---|
| 4,147,990 A * | 4/1979 | Dokus ................. | A61B 5/04004 327/330 |
| 2014/0093853 A1* | 4/2014 | Constantine, III ... | G09B 23/288 434/265 |
| 2015/0282758 A1* | 10/2015 | Chang .................. | A61B 5/6833 600/301 |

* cited by examiner

*Primary Examiner* — Erica Lee
(74) *Attorney, Agent, or Firm* — Andrus Intellectual Property Law, LLP

(57) ABSTRACT

A system for analyzing the energy delivered to ECG device from the defibrillator is disclosed. The system includes an energy analyzing unit configured to measure the energy delivered to the ECG device from the defibrillator, wherein the energy gets diverted to the ECG device during operation of the defibrillator; and a presentation unit capable of presenting the measured energy in the ECG device.

16 Claims, 3 Drawing Sheets

SYSTEM FOR ANALYZING ENERGY DELIVERED TO ECG DEVICE FROM DEFIBRILLATOR

FIELD OF THE INVENTION

The subject matter disclosed herein relates to usage of energy in a defibrillator connected to an ECG device. More specifically the subject matter relates to analyzing the energy delivered to ECG device from the defibrillator.

BACKGROUND OF THE INVENTION

Cardiac related health issues are predominantly increasing among people. Identifying cardiac problems and taking precautionary methods are key factors to manage any exigent conditions that may occur in a cardiac patient. If a situation of cardiac attack occurs the patient can be provided medical therapy for instance using a defibrillator. The defibrillator provides electric energy as a therapeutic dose to the heart for recovering the heart function. Current defibrillators are also capable of monitoring and analyzing electrocardiogram (ECG) data collected from the patient. This data can be used to analyze the functioning of the heart and determine the amount of defibrillation therapy required for the heart. Multiple electrodes may be connected to the patient for obtaining the ECG data. These electrodes may be connected to the chest skin on the patient. A weak electrical signal needs to be transmitted to the patient's body using the electrodes for collecting the ECG data. The energy at the defibrillator may need to be delivered to the patient preferable may be almost 90% of energy need to be given to the patient. In the process remaining 10% energy may leak and then may sometimes get delivered to ECG device or a ECG monitor. However the current devices do not have any mechanism for tracking or determining how much energy is being diverted to the ECG device or the ECG monitor. Thus a user of the defibrillator such as a doctor is not aware of the energy being diverted to the ECG device or the ECG monitor The doctor is also not at present able to determine if right quantity of energy is delivered to the patient to understand the loss in energy.

Accordingly, a need exists for an improved system for analyzing the energy delivered to ECG device from the defibrillator for better consumption of the energy present in the defibrillator.

SUMMARY OF THE INVENTION

The object of the invention is to provide an improved system for analyzing the energy delivered to ECG device from the defibrillator, which overcomes one or more drawbacks of the prior art. This is achieved by a system for analyzing the energy delivered to ECG device from the defibrillator as defined in the independent claim.

One advantage with the disclosed system is that it provides an improved way of utilizing energy generated in a defibrillator connected to an ECG device. Further as the energy utilized is measured the system can determine if enough amount of energy is delivered to the patient for providing defibrillation that can save the life of the patient. Thus alarm signal and other indications provide notifications to a medical expert (nurse or doctor) to identify any fault condition in the ECG device or the ECG monitor.

In an embodiment a system for analyzing the energy delivered to ECG device from the defibrillator is disclosed. The system includes an energy analyzing unit configured to measure the energy diverted to the ECG device from the defibrillator, wherein the energy gets diverted to the ECG device during operation of the defibrillator; and a presentation unit capable of presenting the measured energy in the ECG device.

In another embodiment an ECG device operating with a defibrillator is disclosed. The ECG device comprises an energy analyzing unit configured to measure the energy received from the defibrillator, wherein the energy gets diverted to the ECG device during operation of the defibrillator; and a display device capable of presenting the measured energy to a user.

A more complete understanding of the present invention, as well as further features and advantages thereof, will be obtained by reference to the following detailed description and drawings.

DETAILED DESCRIPTION OF THE INVENTION

In the following detailed description, reference is made to the accompanying drawings that form a part hereof, and in which is shown by way of illustration specific embodiments that may be practiced. These embodiments are described in sufficient detail to enable those skilled in the art to practice the embodiments, and it is to be understood that other embodiments may be utilized and that logical, mechanical and other changes may be made without departing from the scope of the embodiments. The following detailed description is, therefore, not to be taken as limiting the scope of the invention.

As discussed in detail below, embodiments of a system for analyzing the energy delivered to ECG device from the defibrillator is disclosed. The system includes an energy analyzing unit configured to measure the energy diverted to the ECG device from the defibrillator, wherein the energy gets diverted to the ECG device during operation of the defibrillator; and a presentation unit capable of presenting the measured energy in the ECG device.

Figure 1:
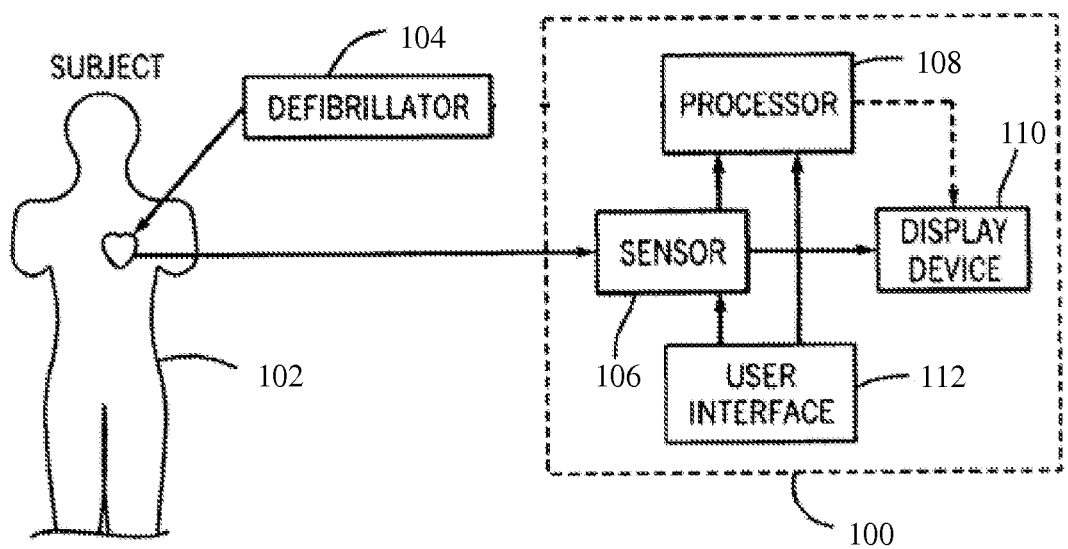
FIG. 1 is a schematic illustration of an apparatus intended to provide a real-time trigger signal from a single channel of an ECG.

Referring to FIG. 1, apparatus 100 is intended to provide a real-time trigger signal from a single channel of an ECG. Such a trigger may be useful in multiple applications where devices must be activated in synchronization with the subject's heart.

FIG. 1 illustrates an example embodiment for heartbeat signal synchronization where an energy pulse is delivered to the heart of subject of interest 102 by a defibrillator device 104 in order to stop an atrial arrhythmia. The pulse may be synchronized to the heartbeat signal to reduce the risk of stimulating the heart into a more dangerous ventricular arrhythmia. In the illustrated embodiment the synchronization pulse is intended to be minimally delayed from the heartbeat of the subject 102. The jitter in timing of the synchronization pulse (variability in precise time relationship of each pulse to the start of the heartbeat) is unimportant since one or very few energy pulses from the defibrillator 104 may be synchronized.

The subject of interest 102 is coupled via a connection for electrocardiographic (ECG) voltage signals, such as electrodes, to the apparatus 100 including a sensor 106, a processor 108, a display device 110, and a user interface 112. While the illustrated example embodiment shows the subject of interest 102 to be a human, in other exemplary embodiments subject of interest 102 may be another living organism, such as a dog, cat, or horse. In still other exemplary embodiments the subject of interest may be non-animal subjects such as simulators used for testing purposes which generate a heartbeat ECG signal for analysis.

The sensor 106, for example an ECG acquisition system, may be composed of isolation circuits, amplifiers, filters, and digitizers of any past, present, or future form known in the art. A digital waveform data stream of ECG data may be passed to the processor 108 where an R-wave synchronization algorithm may be performed.

The processor 108 is generally configured to generate a trigger signal based on a real-time analysis of ECG data and to synchronize and transmit the trigger signal to a medical device, in this case the defibrillator 104, if the heartbeat is normal. The processor 108 may perform this function by generating pulses or other communication indicators which may be output from the monitoring instrument. In various exemplary embodiments, the processor 108 may be any suitable processor capable of processing incoming data with an algorithm and optionally capable of outputting results in a visual or otherwise user-readable format.

The display device 110 may receive indications from the processor 108 that can be combined with the ECG waveform in a way that a human operator of the instrument can confirm that R wave triggers are associated to the appropriate heartbeats in the ECG. If the waveform and trigger display is unsatisfactory, the user may select other ECG leads or reset the algorithm run on the processor 108 to relearn on subsequent heartbeats via the user interface 112. In various exemplary embodiments, the display device 110 may be any suitable display device that can be coupled to the processor 108 and display an ECG waveform.

The energy pulses delivered by the defibrillator 104 may be maximum energy pulses. These energy pulses may put overload onto readable ECG data in the display device 110. The sensor 106 and the display device 110 may require some recovery time due to the overload of the defibrillator 104. Further some energy from the defibrillator 104 is also diverted to the sensor 106.

Figure 2:
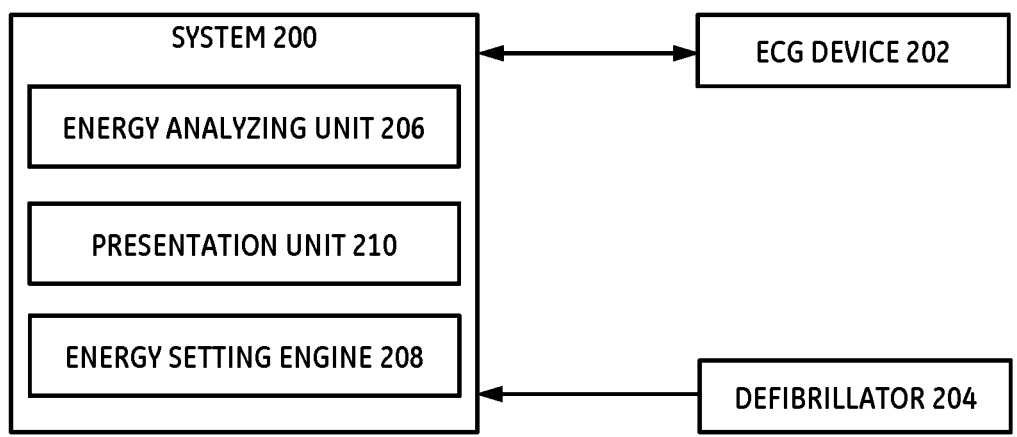
FIG. 2 is a schematic illustration of a system for analyzing the energy diverted to an ECG device from a defibrillator according to an embodiment.

FIG. 2 illustrates a system 200 for analyzing the energy diverted to an ECG device from a defibrillator according to an embodiment. An ECG device 202 gathers ECG data from a patient. The defibrillator 204 delivers therapeutic pulse of electric energy to the heart. A portion of the energy may be diverted to the ECG device 202. This diverted energy is a leakage. The energy diverted needs to be monitored by an energy analyzing unit 206. The energy analyzing unit 206 measures the diverted energy and analyzes. In an embodiment the energy analyzing unit 206 may include multiple components for example electrical components that may be connected to each other. It may be noted that the energy analyzing unit 206 may have any other configuration other than electrical components without limiting from the scope of this disclosure. The energy analyzing unit 206 analyzes the energy to determine if the energy diverted to the ECG device 202 is within a predefined threshold. The predefined threshold may indicate a maximum energy that needs to be delivered to the ECG device 202. In an embodiment an energy setting engine 208 is configured to a set the predefined threshold. The predefined threshold may be set based on user input. In an embodiment 90% of the energy needs to be delivered as the electric pulse to the patient whereas 10% of the energy can get diverted to the ECG device 202 due to leakage. The energy analyzing unit 206 is configured to determine if the energy diverted to the ECG device exceeds 10% of the total energy. If the energy diverted exceeds the predefined threshold then an alarm signal is generated. This indicates that adequate energy is not used for generating the pulses of electrical energy for delivering to the patient rather more energy is diverted. In an instance the energy diverted to the ECG device 202 is presented by a presentation unit 210. Further in another embodiment the energy diverted can be printed from the ECG device 202. The ECG device 202 may have a printing unit (not shown in FIG. 2) that may help in printing information of the diverted energy.

The energy analyzing unit 206 is also configured to set a defibrillator mode for the ECG device 202. In the defibrillator mode the energy analyzing unit 206 measures the energy diverted to the ECG device 202. In an embodiment the energy analyzing unit 206 is also capable of assigning a key for setting the ECG device in the defibrillator mode. The key may be a hard key. In another embodiment the key may be a password provided by the user for changing the ECG device 202 into the defibrillator mode. However the hard key may be any other key that may be used to set the defibrillator mode. The ECG device 202 may need to recover from any energy overload from the defibrillator 204. A recovery time is the time required for recovering and may be the time difference between a first ECG data from the ECG device 202, a defibrillator energy pulse and time for an alarm signal received when the energy diverted to the ECG device 202 exceeds the predefined threshold. The defibrillator overload occurs when the energy diverted to the ECG device 202 exceeds the predefined threshold.

Figure 3:
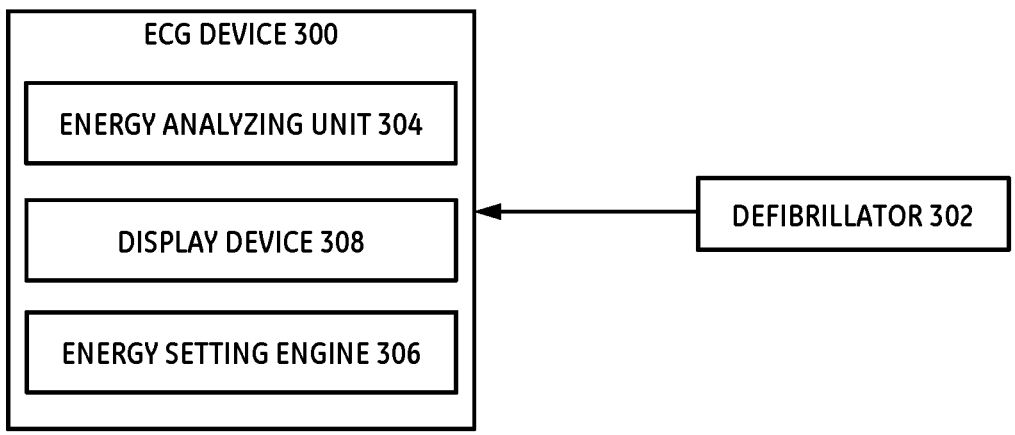
FIG. 3 is a schematic illustration of an ECG device operating with a defibrillator according to an embodiment.

FIG. 3 illustrates an ECG device 300 operating with a defibrillator 302 according to an embodiment. The ECG device 300 is capable of gathering ECG data from a patient. In an embodiment the ECG device 300 may be a usual ECG device or an ECG monitor. As discussed earlier in conjunction with FIG. 2, the defibrillator 302 delivers therapeutic pulse of electric energy to patient's heartA portion of the energy may be diverted to the ECG device 300. The energy diverted needs to be monitored by an energy analyzing unit 304 present in the ECG device 300. In this embodiment the ECG device 300 is capable of monitoring the energy received from the defibrillator 302. The energy analyzing unit 304 measures and analyzes the energy received. In an embodiment the energy analyzing unit 304 may include multiple components for example electrical components that may be connected to each other. It may be noted that the energy analyzing unit 304 may have any other configuration other than electrical components without limiting from scope of this disclosure. The energy analyzing unit 304 analyzes the energy to determine if the energy diverted to the ECG device 300 is within a predefined threshold. The predefined threshold may indicate a maximum energy that can leak and get diverted to the ECG device 300. In an embodiment an energy setting engine 306 is configured to a set the predefined threshold. The predefined threshold may be set based on user input. In an embodiment 90% of the energy needs to be delivered as the electric pulse to the patient whereas 10% of the energy can get diverted to the ECG device 202 due to leakage. The energy analyzing unit 304 is configured to determine if the energy or the energy diverted to the ECG device exceeds 10% of the total energy. If the energy supplied exceeds the predefined threshold then an alarm signal is generated. This indicates that adequate energy is not used for generating the pulses of electrical energy for delivering to the patient rather more energy is diverted to the ECG device 300. In an instance the energy diverted to the ECG device 300 is presented by a display device 308. Further in another embodiment the energy diverted can be printed from the ECG device 300. The ECG device 300 may have a printing unit (not shown in FIG. 3) that may help in printing information of the energy diverted.

The energy analyzing unit 304 is also configured to set a defibrillator mode for the ECG device 300. In the defibrillator mode the ECG device 300 is configured to receive the energy from the defibrillator 302. In this defibrillator mode the energy analyzing unit 304 measures the energy diverted to the ECG device 300. In an embodiment the energy analyzing unit 304 is also capable of assigning a key for setting the ECG device in the defibrillator mode. The key may be a hard key. The key may be a password provided by the user for changing the ECG device 300 into the defibrillator mode. However the hard key may be any other key that may be used to set the defibrillator mode. The ECG device 300 needs to recover from any energy overload from the defibrillator 302. A recovery time is the time required for recovering and may be the time difference between a first ECG data from the ECG device 300, a defibrillator energy pulse and time for an alarm signal received when the energy diverted to the ECG device 300 exceeds the predefined threshold. The defibrillator overload occurs when the energy diverted to the ECG device 300 exceeds the predefined threshold.

Figure 4:
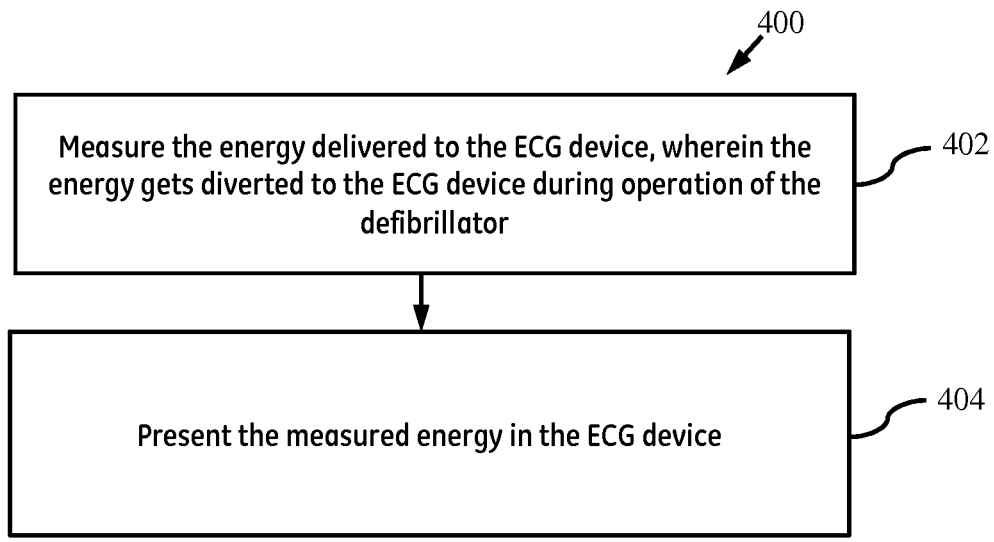
FIG. 4 is a schematic illustration of a block diagram of a method for analyzing energy diverted to an ECG device from a defibrillator according to an embodiment.

Now referring to FIG. 4 illustrating a method 400 for analyzing energy diverted to an ECG device from a defibrillator according to an embodiment. The defibrillator delivers therapeutic pulse of electric energy to patient's heart. In this method, energy diverted to the ECG device due to leakage is measured at block 402. The measured energy is presented through the ECG device at block 404.

Figure 5:
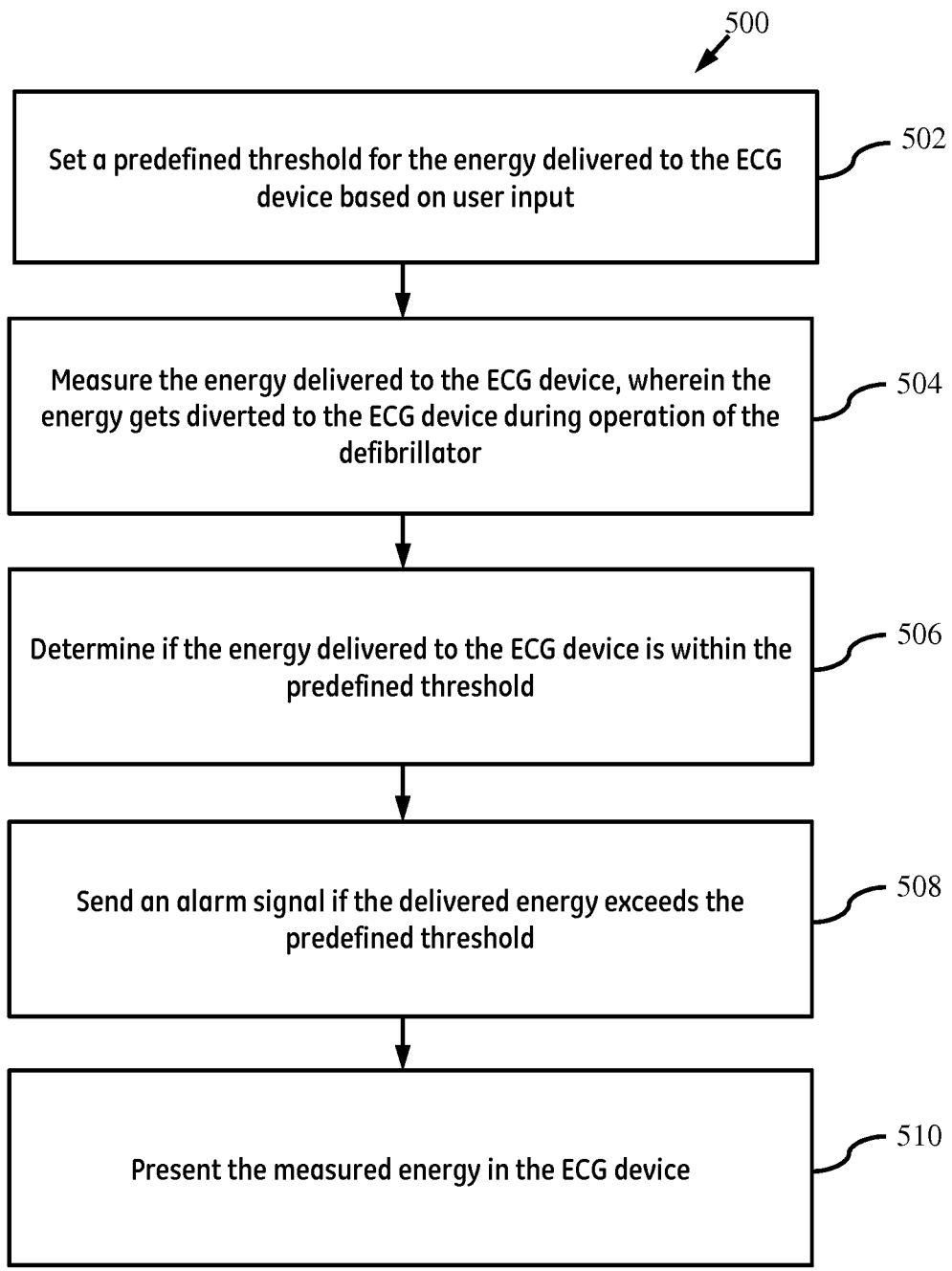
FIG. 5 is a schematic illustration of a block diagram of a method for analyzing energy diverted to an ECG device from a defibrillator according to another embodiment.

FIG. 5 illustrates another method 500 for analyzing energy diverted to an ECG device from a defibrillator according to another embodiment. The method 500 may involve diversion of energy to the ECG device by the defibrillator due to leakage. A predefined threshold for the energy that can be diverted to the ECG device is set at block 502. The predefined threshold may be set based on user input. In an embodiment 90% of energy received at a defibrillator needs to be supplied as electric pulse whereas 10% of energy may get diverted to the ECG device. So the predefined threshold should be 10% of the energy. During operation of the ECG device and the defibrillator the energy diverted to the ECG device is measured at block 504. In an embodiment the energy is measured in a defibrillator mode of the ECG device. The ECG device is set in the defibrillator mode based on user input. Further in another embodiment a key is assigned for setting the ECG device in the defibrillator mode. Then at block 506 it is determined if the energy diverted is within the predefined threshold. If the energy is more than the predefined threshold then an alarm signal is send at block 508. The measured energy is then presented in the ECG device at block 510.

From the foregoing, it will appreciate that the above disclosed a system for analyzing energy delivered to an ECG device from a defibrillator to provide numerous benefits to healthcare enterprises, such as improved way of utilizing energy generated in a defibrillator connected to an ECG device. Further as the energy utilized is measured the system can determine if enough amount of energy is delivered to the patient for providing defibrillation that can save the life of the patient. Thus alarm signal and other indications provide notifications to a medical expert (nurse or doctor) to identify any fault condition in the ECG device or the ECG monitor.

This written description uses examples to disclose the invention, including the best mode, and also to enable any person skilled in the art to practice the invention, including making and using any computing system or systems and performing any incorporated methods. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal language of the claims.

I claim:

1. A system for analyzing energy delivered to an ECG device from a defibrillator, the system comprising:
   an energy analyzing unit configured to measure the energy diverted to the ECG device from the defibrillator;
   wherein the diverted energy is a portion of a total energy outputted by the defibrillator and is diverted to the ECG device rather than delivered as a therapeutic pulse to a subject; and
   a presentation unit configured to present the diverted energy measurement.

2. The system of claim 1, wherein the energy analyzing unit is further configured to measure a recovery time of the ECG device from an energy overload from the defibrillator.

3. The system of claim 1, further comprises an energy setting engine configured to set a predefined threshold for the energy diverted to the ECG device based on user input.

4. The system of claim 3, wherein the energy analyzing unit is further configured to:
   determine if the energy diverted to the ECG device is within the predefined threshold; and
   send an alarm signal if the diverted energy measurement exceeds the predefined threshold.

5. The system of claim 1, wherein the energy analyzing unit is further configured to set a defibrillator mode for the ECG device, wherein in the defibrillator mode the energy analyzing unit measures the diverted energy to the ECG device.

6. The system of claim 5, wherein the energy analyzing unit is configured to assign a key for setting the ECG device in the defibrillator mode.

7. An ECG device operating with a defibrillator, the ECG device comprising:
   an energy analyzing unit configured to measure the energy diverted from the defibrillator, wherein the diverted energy is a portion of a total energy outputted by the defibrillator and is diverted to the ECG device rather than delivered as therapeutic pulse to a subject; and
   a display device configured to present the diverted energy measurement.

8. The ECG device of claim 7, wherein the energy analyzing unit is further configured to measure a recovery time of the ECG device from an energy overload from the defibrillator.

9. The ECG device of claim further comprises an energy setting engine configured to set a predefined threshold for the diverted energy received from the defibrillator based on user input.

10. The ECG device of claim 9, wherein the energy analyzing unit is further configured to:
   determine if the diverted energy received from the defibrillator is within the predefined threshold; and
   send an alarm signal if the diverted energy exceeds the predefined threshold.

11. The ECG device of claim 7, wherein the energy analyzing unit is further configured to set a defibrillator mode, wherein the energy analyzing unit measures the diverted energy received from the defibrillator when the ECG device is in the defibrillator mode.

12. The ECG device of claim 11, wherein the energy analyzing unit is further configured to assign a key for setting the ECG device in the defibrillator mode.

13. The ECG device of claim 7, wherein the ECG device is one of an ECG diagnostic device and an ECG monitor.

14. A method for analyzing energy delivered to an ECG device from a defibrillator, the method comprising:
   measuring the energy diverted to the ECG device with an energy analyzing unit, wherein the diverted energy is a portion of a total energy outputted by the defibrillator and is diverted to the ECG device rather than delivered as therapeutic pulse to a subject; and
   presenting the diverted energy measurement on a display device associated with the ECG device.

15. The method of claim 14 further comprising:
   setting a predefined threshold for the diverted energy to the ECG device based on user input;
   determining if the diverted energy to the ECG device is within the predefined threshold; and
   sending an alarm signal if the diverted energy measurement exceeds the predefined threshold.

16. The method of claim 14 further comprising:
   setting a defibrillator mode for the ECG device, wherein in the defibrillator mode the energy analyzing unit measures the diverted energy to the ECG device; and
   assigning a key for setting the ECG device in the defibrillator mode.

* * * * *